United States Patent [19]

Van Aken Redinger et al.

[11] 4,455,691
[45] Jun. 26, 1984

[54] SILICONE GEL FILLED PROSTHESIS

[75] Inventors: Peter Van Aken Redinger; Richard A. Compton, both of Santa Barbara, Calif.

[73] Assignee: Minnesota Mining and Manufacturing Company, St. Paul, Minn.

[21] Appl. No.: 81,379

[22] Filed: Oct. 3, 1979

[51] Int. Cl.³ .............................................. A61F 1/00
[52] U.S. Cl. ........................................ 3/36; 428/447; 528/42; 528/901
[58] Field of Search .............. 3/36; 428/447; 426/127; 528/42, 901

[56] References Cited

U.S. PATENT DOCUMENTS

| | | | |
|---|---|---|---|
| 2,842,775 | 7/1958 | Pangman | 3/36 |
| 3,020,260 | 2/1962 | Nelson | 528/15 |
| 3,179,619 | 4/1965 | Brown | 260/37 FB |
| 3,189,921 | 6/1965 | Pangman | 3/36 |
| 3,293,663 | 12/1966 | Cronin | 3/36 |
| 3,366,975 | 2/1968 | Pangman | 3/36 |
| 3,416,160 | 12/1968 | Arion | 3/36 |
| 3,683,424 | 8/1972 | Pangman | 3/36 |
| 3,775,452 | 11/1973 | Karstedt . | |
| 3,779,987 | 12/1973 | Razzano . | |
| 3,801,544 | 4/1974 | Mink et al. . | |
| 3,845,507 | 11/1974 | Kirby et al. | 3/36 |
| 3,883,902 | 5/1975 | Lynch | 3/36 |
| 3,884,866 | 5/1975 | Jeram et al. . | |
| 3,911,503 | 10/1975 | Hankin | 3/36 |
| 3,919,724 | 11/1975 | Sanders et al. | 3/36 |
| 3,934,274 | 1/1976 | Hartley, Jr. | 3/36 |
| 3,957,713 | 5/1976 | Jeram et al. . | |
| 4,029,629 | 6/1977 | Jeram . | |
| 4,072,635 | 2/1978 | Jeram . | |
| 4,095,295 | 6/1978 | Lake | 3/36 |
| 4,100,627 | 7/1978 | Brill | 3/36 |
| 4,138,382 | 2/1979 | Polmanteer . | |

FOREIGN PATENT DOCUMENTS 774531 12/1967 Canada ........................................ 3/1

OTHER PUBLICATIONS

"Natrashiel Mammary Implant", McGhan Medical Corporation, 700 Ward Dr., Santa Barbara, CA, Sheet No. 120388, 10/78, 2 pages.
"Intrashiel Mammary Implant", McGhan Medical Corporation, 700 Ward Dr., Santa Barbara, CA, 2 pages (no date).
"Blood Compatibility of Methyl, Methyl Vinyl, Methyl Phenyl, and Trifluoropropylmethylvinyl Silicone Rubber without Silica Fillers in the Spiral-Coiled Membrane Lung", by T. Kolobow et al., *J. Biomed. Mater. Res.*, vol. 11, pp. 471–481 (1977).
"Superior Blood Compatibility of Silicone Rubber Free of Silica Filler in the Membrane Lung", by T. Kolobow et al., vol. XX, Trans. Amer. Soc. Artif. Int. Organs, pp. 269–276 (1974).
"Natrashiel II Mammary Implant", McGhan Medical Corporation, 700 Ward Dr., Santa Barbara, CA, 93111, copyright 1978.
"In vivo Tissue Reactivity of Radiation-Cured Silicone Rubber Implants", by Gifford et al., *Journal of Biomedical Materials Res.*, vol. 10, pp. 857–865 (1976).
"Bleeding of Silicone From Bag-Gel Breast Implants and Its Clinical Relation to Fibrous Capsule Reaction", by Barker et al., *Plastic & Reconstructive Surgery*, Jun. 1976 (vol. 61, No. 6), pp. 836–841.
"Foreign-Body Reaction to Silicone Gel in Axillary Lymph Nodes After an Augmentation Mammaplasty", by Hausner et al., *Plastic & Reconstructive Surgery*, Sep. 1978 (vol. 62, No. 3), pp. 381–384.

*Primary Examiner*—Clifford D. Crowder
*Attorney, Agent, or Firm*—Donald M. Sell; James A. Smith; Jennie G. Boeder

[57] ABSTRACT

A prosthesis for subcutaneous implantation in a patient comprising a flexible sac and a silicone gel contained within the sac. The wall of the sac is comprised of at least one continuous layer of silicone elastomer which substantially impedes the migration of said silicone gel from the sac.

12 Claims, 3 Drawing Figures

SILICONE GEL FILLED PROSTHESIS

This invention relates to a silicone gel filled flexible prosthesis for subcutaneous implantation in a patient. More particularly it relates to a gel filled prosthesis having a sac wall which impedes migration of the silicone gel from the prosthesis.

Because the morale of persons with small breasts and patients who have undergone a mastectomy is usually very low, a number of methods have been developed to increase or restore the body form and contour. One such method involves the subcutaneous implantation of breast prostheses. A second method involves the use of external breast prosthesis.

The external breast prostheses are comprised of silicone rubber containers with silicone gel fillings. The container walls are usually comprised of a thick silicone elastomer in order to provide the required integrity for continuous handling which the prosthesis is subjected, e.g., U.S. Pat. No. 4,100,627. Such thick wall prostheses are undesirable for subcutaneous implantation because of the unnatural feel which the thick walls impart to the overlying skin.

Early implantable breast prostheses were usually made of plastic sponge material such as polyurethane or polyvinyl chloride. Such materials were largely unsatisfactory because with time they were invaded by body tissue and fluids and then tended to shrink and become hard and unyielding.

An early improvement was provided by Pangman in U.S. Pat. Nos. 2,842,775, 3,189,921 and 3,366,975 wherein he encapsulated much of the bulk of the prosthesis material within a more or less inert, impermeable sac or membrane thereby preventing invasion, degradation, shrinkage or hardening of the encapsulated filling. Unfortunately, in all three patented constructions, Pangman provided an outer prosthesis covering of foam; first, polyvinyl chloride; next, polyurethane; and finally, polyurethane or polyether. The outer layer of foam was intended to permanently fix the position of the prostheses through provision for ingrowth of attachment tissue. Pangman's devices reduced the problem of shrinkage and hardening of a mammary implant but with time, the ingrowth of tissue into the outer foam layer provided for development of a hard encapsulation which was still objectionable.

Cronin, in U.S. Pat. No. 3,293,663, discloses a porous attachment material only on the back wall of his device so that theoretically there should be little or no hard tissue formation over the other surfaces of the prosthesis. Cronin used a flexible sac made of biologically inert silicone rubber filled with soft yieldable silicone gel.

One prevalent problem that was found in the use of flexible silicone sacs and gels is that fibrous contraction has still been found to occur in from 5 to 40% of patients after implantation. Although the problem is much reduced from that which occurred with the early foam implants and the later foam covered implants, the problem still remains.

The role of silicone gel or oil, if any, in fibrous contraction is still unclear yet it is the belief of many surgeons that the main liability of currently available gel implants is the gel bleed detectable at the implant surface. Many surgeons feel that the reduction of silicone gel or oil migration into surrounding tissue, however minute, would be a definite improvement, see "Bleeding of Silicone From Bag-Gel Breast Implants and Its Clinical Relation to Fibrous Capsule Reaction", by Baker et al, *Plastic & Reconstructive Surgery* June 1976 (Vol. 61, No. 6); "Foreign-Body Reaction to Silicone Gel in Axillary Lymph Nodes After an Augmentation Mammaplasty" by Hausner et al, *Plastic & Reconstructive Surgery*, September, 1978 (Vol. 62, No. 3).

The silicone gel or oil migration is also believed to cause the wall to change volume (i.e., swell). Swelling of the elastomeric material has long been associated with the decrease in the tensile strength and elongation properties of the elastomeric materials, see *Principles of Polymer Chemistry* by Paul J. Flory (Cornell Press 1975) pp. 492-493. This decreases in these properties increases the potential for a complete rupture of the sac walls.

The present invention substantially impedes the migration of the silicone gel and/or oil through the sac walls thus preserving the tensile and elongation properties of the sac of the prostheses. This impedement is accomplished in the present invention while simultaneously utilizing a thin sac wall which allows the present invention to provide an almost natural feel once implanted.

The present invention is a prosthesis for subcutaneous implantation in a patient comprising a flexible sac and a silicone gel contained within the sac. The wall of the sac is between 0.05 mm and about 0.2 mm in thickness. The wall is comprised of a layer of silicone elastomer which substantially impedes the migration of the silicone gel from the sac. This layer is at least 0.025 mm in thickness and experiences a weight increase of less than 10% when tested in accordance with ASTM D471 utilizing a dimethylpolysiloxane test gel having a 300 centistoke viscosity.

The preferred dimethylpolysiloxane test gel is comprised of 8 parts by weight

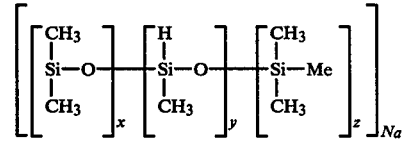

and 92 parts by weight

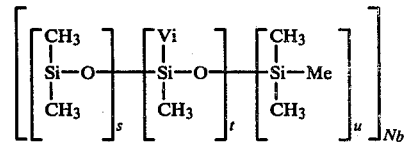

wherein $s=162$, $t=1$, $u=2$, $x=172$, $y=6$, $z=2$, $N_a=180$ and $N_b=165$.

The wall of the sac may also be a composite structure of a plurality of silicone elastomers or mixtures of silicone elastomers which have a total thickness of between about 0.05 and about 0.2 mm wherein at least one layer of the total composite wall is at least 0.025 mm in thickness and is made of a silicone elastomer which has a weight increase of less than 10% when tested in accordance with ASTM D471 utilizing the above stated dimethylpolysiloxane test gel having a 300 centistoke viscosity.

BRIEF DESCRIPTION OF THE DRAWINGS

Understanding of the invention will be aided by reference to the accompanying drawing in which like numbers refer to like parts in the several views, and in which.

Figure 1:
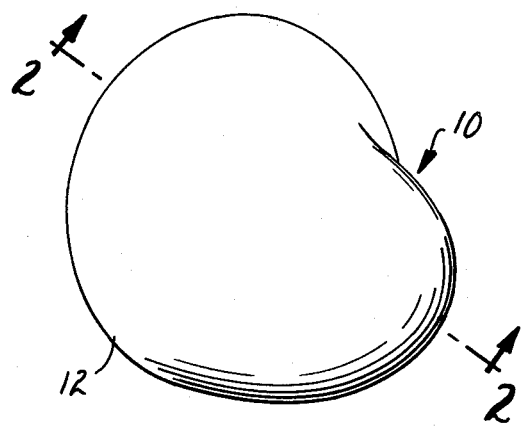
FIG. 1 is perspective view of the mammary prosthesis of the present invention.

Referring now to the drawings, the prosthesis indicated generally as 10, is comprised of a flexible sac 12 and a silicone gel 14.

Figures 2, 3:
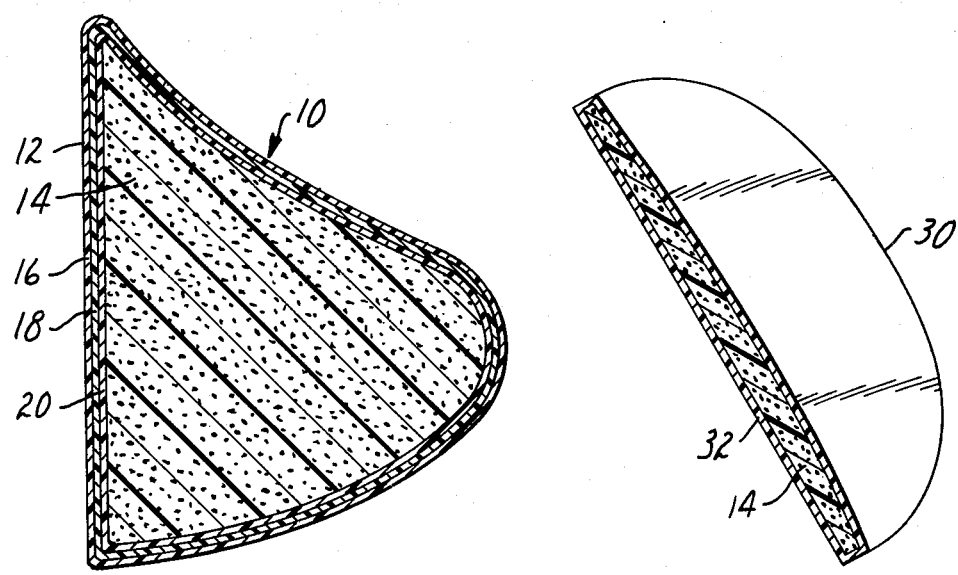
FIG. 2 is a cross-sectional view through line 2—2 of the prosthesis shown in FIG. 1.
FIG. 3 is a perspective view of an alternative prosthesis in accordance with the present invention, with portions thereof broken away.

As can be best seen in FIG. 2, the wall of sac 12 is of a composite nature and is comprised of a first continuous layer 16, a second continuous layer 18 and a third continuous layer 20. Although either of the three layers can be made to impede the migration of silicone gel through the sac 12, it is preferred that the second layer 18 be constituted to do so by the means which are discussed below.

The silicone elastomers utilized for first and third continuous layers, 16 and 20, may be homopolymers such as polydimethylsiloxane or polymethylvinylsiloxane or they can be copolymers such as copolymers of methylvinylsiloxane and dimethylsiloxane. The preferred silicone elastomer is a heteropolymer of diphenylpolysiloxane and dimethylpolysiloxane having 3-7 mole percent diphenyl polysiloxane substituents.

The silicone elastomer of layers 16 and 20 may also contain fillers, such as reinforcing silica filler, processing aids, additives, pigments. The fillers may be present in amounts of up to 70 parts per hundred by weight. The silicone elastomers are endblocked with conventional endblocking units present at levels of less than 4 mole percent. Examples of such endblocking units are dimethylvinylsiloxane units, trimethylsiloxy units, methylphenylvinylsiloxy units or hydroxyl units. In the present invention, 0.133 mole percent dimethylvinylsiloxane units is preferred for this purpose.

The silicone elastomer can be vulcanized by conventional means, such as with organic peroxides, electromagnetic radiation, or by using a polysiloxane crosslinker containing silicone-bonded hydrogen atoms with a vinyl containing siloxane elastomers and a platinum catalyst. In the present invention it is preferred that a platinum catalyst formed by dissolving hexachloroplatinic acid tetravinylcyclotetrasiloxane in isopropyl alcohol be used.

Second layer 18 is a silicone elastomer which when cured has a weight increase of less than 10% when tested in accordance with ASTM D471 utilizing the aforementioned dimethylpolysiloxane test gel having a 300 centistoke viscosity. It has been found that weight increases which are less than 10% minimize the potential for the reduction of the tensile and elongation properties which has been attributed to silicone gel migration through the sac walls.

The silicone elastomer of second layer 18 is preferrably composed of reaction product of dimethylpolysiloxane and either 3,3,3,-trifluoropropylpolysiloxane, diphenylpolysiloxane or methylphenylpolysiloxane. The final reaction product preferably contains about 8 to about 50 mole percent diphenylpolysiloxane substituents, with about 15 to about 30 being preferred, at least 90 mole percent methyl 3,3,3-trifluoropropylpolysiloxane substituents or at least 30 mole percent methylphenylpolysiloxane substituents. It is contemplated that the silicone elastomer which acts a barrier to migration may also be a reaction product of dimethylpolysiloxane and siloxane elastomer which has a combination of the aforementioned substituents e.g. diphenylpolysiloxane and 3,3,3-trifluoropropylpolysiloxane.

The silicone elastomers of second layer 18 are endblocked with the conventional endblocking units used in layers 16 and 20 at levels of less than 4 mole percent. In the present invention, 0.133 mole percent dimethylvinylsiloxane units is preferred for this purpose.

The silicone elastomer of second layer 18 can also contain fillers, such as reinforcing silica filler, processing aids, additives and pigments. The filler may be present in about 15 to about 70 parts per hundred by weight. The silicone elastomer can be vulcanized by conventional means, such as with organic peroxides, electromagnetic radiation, or by using a polysiloxane crosslinker containing silicone-bonded hydrogen atoms with a vinyl containing siloxane elastomers and a platinum catalyst. In the present invention it is preferred that the same platinum catalyst utilized for layers 16 and 20 above be utilized in second layer 18.

The silicone gel 14 is a normally crosslinked dimethypolysiloxane which are generally known to the art, e.g., U.S. Pat. No. 3,020,260. The preferred gel is comprised of about 5-20 parts by weight, with 8 parts by weight being preferred of

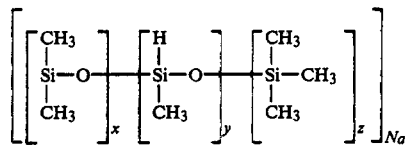

and from 80 to about 95 parts by weight, with 92 parts by weight being preferred of

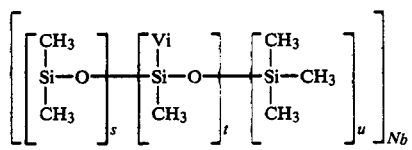

wherein $S=162$, $t=1$, $u=2$, $x=172$, $y=6$, $z=2$, $N_a=180$ and $N_b=165$. A catalytic amount, about 5 to about 50 parts per million by weight, of a platinum catalyst used in layers 16, 18 or 20 is present. The vulcanization may be accelerated by exposing the gel to a temperature of 150° C. for 2 to 3 hours.

The wall of sac 12 is formed to be between about 0.05 mm and 0.2 mm (0.002 inch to 0.008 inch) in thickness. When the wall of sac 12 is a composite structure, it is preferred that second layer 18 be between 0.025 mm and 0.05 mm (0.001 inch and 0.002 inch) in thickness. It will be recognized by one skilled in the art that the silicone elastomer that makes up the second layer 18 may be utilized in first or third continuous layers, 16 or 20, and still effectively impede the migration of this silicone gel 14. Alternatively the silicone elastomer that constitutes second continuous layer 18 of sac 12 may constitute the entire wall of a prosthesis. Such an alternative prosthesis 30 having a sac 32 and gel 14 is depicted in FIG. 3.

The prosthesis of the present invention may be made by first making a sac. To form the sac, dispersions of the above stated unvulcanized elastomeric material in solvents which can be totally evaporated from the final product at low temperatures e.g., 25° C. are made. When the silicone elastomer contains diphenylpolysiloxane substituents the solvents may be any aromatic or linear aliphatic of $C_6$ or greater. If the silicone elastomer contains trifluoropropylpolysiloxane substituents, the preferred solvents are ketones. The prosthesis sac is prepared by dipping a mandrel which is shaped to the desired form into a dispersions of unvulcanized silicone elastomer which constitutes third continuous layer 20. The coated mandrel is removed and the solvent allowed to evaporate. The coated mandrel is then dipped into the dispersed elastomer which constitutes second continuous layer 18. The coated mandrel may then be dipped into either of the elastomeric dispersions so as to form the desired composite structure. The solvent is allowed to evaporate after each coating. All coats are preferably cured together after the coating has been built up to yield the desired post-cure thickness of between 0.05 mm and 0.2 mm. At this thickness the cured shell is soft, flexible and preferentially elastic. Although the curing may occur at room temperature, it is preferably accelerated by the use of an air circulating oven.

After the silicone elastomer sac has been cured, it is removed from the mandrel by stretching the hole at the mandrel attachment site. The hole is then sealed by cementing a patch of the same type of cured silicone elastomer over and overlapping the periphery of the hole.

Subsequently, uncured and hence liquid silicone gel is injected with the aid of a hypodermic needle through the lined sac and then thermally cured to its desired firmness. Prior to curing the hypodermic entrance may be sealed by applying a dimethylpolysiloxane having an alkoxy or oxime curing system, e.g., Dow Corning 92009, a room temperature vulcanizing adhesive.

Alternatively a shell can be formed by the dipping process described above of only the elastomeric materials of first continuous layer 16. A coating dispersion of a silicone elastomer which when cured has a weight increase of less than 10% when tested in accordance with ASTM D471 utilizing a dimethylpolysiloxane test gel having 300 centistoke viscosity is then prepared.

The coating dispersion is injected into the cured sac with a hypodermic needle and then slush-coated, i.e., evenly swirled over the inside of the inflated shell. The coated shell is then placed in an oven and the solvent evaporated through the sac wall providing an adherent vulcanized film of elastomers on the inside of the sac. It has been observed that adhesion is not a problem in that the layer appears to fuse tightly to the outer layer during the vulcanization, almost regardless of the elastomer used for the coating.

The above described procedures are preferentially used for preparation of stemless valve-less prostheses of a variety of sizes and shapes. These procedures are also applicable to other augmentation prostheses which have shapes which are spherical, ellipsoidal, rounded top with flattened base, etc. (see FIG. 3). It is also contemplated that the silicone gel impeding layer could be advantageously used for prosthetic devices of various other designs having, e.g., valves or filling openings providing only that such devices are intended for use with silicone gel or silicone oil. It is not intended that the invention be limited by the type or extent of external tissue attachment means which may be affixed to the device.

The following examples are illustrative only and should not be construed as limiting the present invention which is properly delineated in the claims. All parts are parts by weight unless otherwise stated and all viscosities taken with a Brookfield viscometer at 25° C. unless otherwise stated:

EXAMPLE 1

An implantable mammary prosthesis was prepared by dipping a mandrel into two different silicone elastomer dispersions as disclosed below:

The first dispersion was prepared by mixing three reaction products A, B and C. Part A was prepared by adding 2808 grams octamethyltetracyclosiloxane, 396 grams octaphenyltetracyclosiloxane, 4.96 grams divinyltetramethyldisiloxane to a 4000 ml flask. The material was heated to 150° C. at which time 2 grams of finely ground potassium hydroxide was added. After 4 hours of heating, the material had a (Brookfield) viscosity of 100,000 cp at 25° C. The material was cooled to room temperature and $CO_2$ was bubbled thru the viscous material. Next, 1100 grams of this material was added to a size 4 Baker-Perkins mixer with sigma blades (manufactured by Baker-Perkins of Saginaw, Mich.), along with 20 grams hexamethyldisiloxane and 250 grams of silica (Cabot MS.7 available from the Cabot Corp. of Boston, Mass.). The silica was mixed into the polymer, vacuum applied to the mixer to 10 mm Hg. The polymer was heated to 150° C. The material was mixed under these conditions for 4 hours. At this time the heat and vacuum were removed. One thousand grams of xylene were added to the mixer dispersing the elastomer. The resulting dispersed elastomer had a viscosity of approximately 1000 cp.

Part B A hydride containing polymer was the product of the following reaction: Into a 3000 ml flask was added 1406 grams octamethyltetracyclosiloxane, 592 grams of methylhydrogen polysiloxane, i.e., Dow Corning 1107 fluid, 108 grams hexamethyldisiloxane, 3.8 ml conc. $H_2SO_4$. With agitation these materials were heated to 120° C. for 3 hours. At the onset of heating, 10 grams powdered carbon black was added. The reaction product was filtered to remove all carbon black. The filtered material was placed into a 3000 ml flask outfitted for vacuum distillation. The material was heated to 190° C. with 2 mm Hg vacuum. Approximately 300 ml of the siloxane volatile was stripped from the polymer. The polymer remaining in the flask had a viscosity of 40 cp.

Part C A platinum catalyst was the product of the following reaction: To a 500 ml flask was added 5 gm. hexachloroplatinic acid, 142.8 gm. tetramethyltetravinyltetracyclosiloxane, 200 gm. isopropyl alcohol with agitation and a slight $N^2$ purge. The flask was placed under vacuum to 20 mm Hg. The flask was heated to 80° C. and remained so until all isopropyl alcohol was removed from the flask. The resulting complex had a platinum content of 3.5%.

The first dispersion consisted of:
2750 grams xylene
2250 grams Part A
25 grams Part B
12 drops Part C A second dispersion was made as follows: Part $A_2$ was made by placing in a 4000 ml flask 1771 grams octamethyltetracyclosiloxane, 1188 grams octaphenyltetracyclosiloxane, 5.5 gm. divinyltetramethyldisiloxane. These reactants were heated to 160° C. and 4 gm. of finely ground KOH was added. After 12 hours, the material had a viscosity of 95,000 cp. Eleven hundred grams of this polymer were added to the Baker-Perkins type mixer along with 20 gm. hexamethyldisiloxane, and 250 gm. silica (Cabot MS.7). The mixing conditions were the same as described for the first dispersion. One thousand grams of xylene were added to the elastomer so as to create a dispersion.

The second dispersion was made by mixing:
2750 grams xylene
2250 grams Part $A_2$
25 grams of Part B of the first dispersion
12 drops of Part C of the first dispersion Polyester mandrels of a breast type shape were dipped into the second dispersion described above. A stream of 100° C. air was blown across the surface of the mandrel so as to evaporate a partial amount of solvent. After 10 mins. the mandrel was dipped into the first described dispersed elastomer, and left to sit under the stream of 100° C. air. Subsequent dip coats were applied to the first described dispersed elastomer until an overall thickness of 0.152 mm (0.006 inches) was created. The mandrel was placed into a circulation oven at 150° C. for 30 minutes. The vulcanized shell was removed from the mandrel by stretching the hole at the mandrel attachment side. The hole was then sealed by vulcanizing a patch of the same second described elastomer, over and overlapping the periphery of the hole. The above described shell was filled with a silicone gel.

Silicone gel was prepared by mixing three reaction products. Part 1 was prepared by adding 2,901.0 grams octamethyltetracyclosiloxane, 25.8 grams tetramethyltetravinyltetracyclosiloxane, 39.27 grams hexamethyldisiloxane and 3.8 ml concentrated sulfuric acid into a 4,000 ml flask. With agitation these materials were heated to 120° C. for three hours. At the onset of heating, 10 grams powdered carbon black was added. The reaction product was filtered to remove all carbon black. The filtered material was placed into a 4,000 ml flask outfitted for vacuum distillation. The material was heated to 190° C. with 2 mm mercury vacuum. Approximately 400 ml of the siloxane volatiles was stripped from the polymer. The polymer remaining in the flask had a viscosity of 220 centipoise.

Part 2. A hydride containing polymer was made by reacting in a 3,000 ml flask 2,128.7 grams octamethyl tetracyclosiloxane, 54 grams of methylhydrogenpolysiloxane, i.e. Dow Corning, 1107 fluid, 27 grams hexamethyl disiloxane, 3.8 ml concentrated $H_2 SO_4$. With agitation these materials were heated to 120° C. for three hours. At the onset of heating 10 grams powdered carbon black was added. The reaction product was filtered to remove all carbon black. The filtered material was placed into a 3,000 ml flask outfitted for vacuum distillation. The material was heated to 190° C. with 2 mm mercury vacuum. Approximately 300 ml of siloxane volatiles was removed from the polymer. The polymer remaining in the flask had a viscosity of 260 centipoise.

A platinum catalyst was prepared as outlined in Part C of the first dispersion. The gel consists of 92 parts per 100 Part 1, 8 parts per 100 Part 2, and 10 parts per million platinum catalyst.

The above described prosthesis was tested for gel bleed against a prosthesis whose wall construction was made only of the first described elastomer (hereinafter referred to as the standard prosthesis), by placing the prostheses onto an accurately weighed filter paper (Medium 2832, Grade 615, 15 cm. diameter sold by Van Waters and Rogers, Inc. of Norwalk, Calif.). At the end of 110 days the weight gain of the filter paper on which of the standard prosthesis was placed was 0.115 gram. The weight gain of the filter paper on which the prosthesis with the first dip of the second dispersion was placed was 0.005 grams.

EXAMPLE 2

An implantable prosthesis was prepared by dipping a mandrel described in Example 1 into the first dispersed elastomer described in Example 1. Sufficient dips were performed with 10 minutes of 100° C. air exposure between dips so as to build a shell thickness of 0.152 mm (0.006 inches). Upon vulcanization as per Example 1 the shell was removed from the mandrel and a patch applied per Example 1.

Into this sealed shell there was injected a dispersion consisting of 87 parts ethyl ketone, 1 part of the hydride containing polymer described in Example 1, 12 parts Dow Corning 422 stock, a fluorosilicone rubber compounding base consisting of trifluoropropyl methyl vinyl polysiloxane polymer (84% by weight) and a reinforcing silica (16% by weight) available from Dow Corning of Midland, Mich. In addition 10 ppm platinum was added as described in Example 1. Thirty cubic centimeters of the described dispersion was injected into the mammary prosthesis via syringe. The shell was rotated slowly by hand so as to provide a continuous layer on the inside surface of the mammary shell. Upon even coating the prosthesis was placed into a circulating oven at 150° C. for 30 minutes. Upon removal all traces of ketone solvent, the dispersion had vulcanized to the inside walls of the shell. The prosthesis was then injected with a gel material as described in Example 1.

This prosthesis was tested similarly to Example 1. The weight gain of the filter paper upon which was placed the standard prosthesis for 100 days was 0.102 grams. The weight gain of the filter paper upon which was placed the prosthesis coated with the fluoroelastomer dispersion was 0.004 grams.

EXAMPLE 3

Sheets of elastomers were prepared from the product of copolymerization of octaphenyltetracyclosiloxane and octamethyltetracyclosiloxane with vinyl endblocking as described in Example 1. The polymers were filled with a silica (Cabot MS.7) and crosslinked with a hydride containing polymer as per Example 1 including the platinum per Example 1. Varying amounts of octaphenyltetracyclosiloxane were used as described below and the degree of polymerization was changed. The following polymers were prepared.

Mole % diphenylsiloxy groups and degree of polymerization:

| # | % | Degree of Polymerization |
|---|---|---|
| 1 | 8 | 1500 |
| 2 | 10 | 1000 |

-continued

| # | % | Degree of Polymerization |
|---|-----|------|
| 3 | 12  | 1500 |
| 4 | 15  | 1200 |
| 5 | 17  | 1200 |
| 6 | 20  | 1000 |
| 7 | 25  | 1000 |
| 8 | 50  | 750  |

The test method as specified by ASTM D471 was followed. The immersion fluid was a dimethylsiloxane test gel disclosed above.

For percent weight change measurements, rectangles, 25.4 mm×50.8 mm×2.03 mm×0.127 mm (1"×2"×0.080"+0.005") were prepared from cured elastomer sheets. The rectangles were weighed in air to the nearest mg. The rectangles were then placed in individual ml beakers containing the dimethylsiloxane test gel. The beakers were then placed in a 110° C. oven for 22 hours.

Following the experimental conditions the samples were allowed to cool for 1½ hours. The rectangles were removed and placed on lint free filter paper disclosed in Example 1. Excess test gel was removed with a wooden spatula. The samples were then briefly immersed in acetone to remove excess surface test gel and gently blotted with filter paper.

Following the above cleaning the rectangles were again washed dried in air.

The following weight changes were observed:

| Sample | Mole Percent Diphenylsiloxy Groups | % Weight Change |
|--------|-------|---------|
| 1 | 8     | +11.22 |
| 2 | 10    | +6.82  |
| 3 | 12    | +2.33  |
| 4 | 15    | −1.86  |
| 5 | 17    | −4.80  |
| 6 | 20    | −5.83  |
| 7 | 25    | −8.64  |
| 8 | 50    | −27.08 |
| 9 | LS 422 | −1.46 |

These results indicate that as the mole percent diphenylsiloxy units increase the ability of the test gel to migrate into the vulcanized samples is reduced. This indicates that high diphenyl containing vulcanizate would impede the migration of dimethyl gels. Negative values further indicate that there may be established a mole percent diphenol content at which the exchange of molecular species yields no weight change.

EXAMPLE 4

To compare the rate and amounts of diffused dimethylpolysiloxane gel through prosthesis sacs containing a composition of matter which impedes migration, filter paper as disclosed in Example 1 was weighed on an analytical balance to the nearest Mg. Samples were prepared via the following procedure: Mandrel dipping was performed in environmentally controlled class 1,000 cleanrooms. The barrier coated samples were first dipped into a silicone elastomer (barrier coat) which demonstrated low swell in dimethyl siloxane test gel per Example 3. Upon partial evaporation of the solvent, subsequent coats of standard silicone rubber were applied, building to the desired thickness. The sacs were then heat vulcanized at 150° C. for 30 minutes in a hot air oven. Control shells were fabricated via the same procedure deleting the first dip into the barrier coat elastomer. Thickness of the barrier mammary shells and standard shells were consistent. Patch material used on the barrier shells was fabricated in a fashion such that the inside facing surface material is the low soluble barrier rubber. Silicon gel as described in Example 1 was injected into the samples and heat vulcanized at 150° C. for 5 hours in the hot air oven. The samples were placed on the pre-weighed filter paper of Example 1 to collect any diffusing dimethyl gel.

Weights of the filter paper were obtained at intervals listed in Table I.

TABLE I
VIII. TEST RESULTS

| | | | | |
|---|---|---|---|---|
| 1. Barrier Shell #1 | 24 | 63 | 85 | 111 |
| Elapsed Time (days) | 0.0009 | 0.0023 | 0.0018 | 0.0053 |
| Measured Bleed (grams) | | | | |
| 2. Barrier Shell #2 | 24 | 63 | 85 | 111 |
| Elapsed Time (days) | 0.0010 | 0.0034 | 0.0021 | 0.0063 |
| Measured Bleed (grams) | | | | |
| 3. Barrier Shell #3 | 33 | 75 | 97 | 119 |
| Elapsed Time (days) | 0.0008 | 0.0028 | 0.0025 | 0.0039 |
| Measured Bleed (grams) | | | | |
| 4. Averages | 27 | 67 | 89 | 114 |
| for Barrier Shells | 0.0009 | 0.0028 | 0.0021 | 0.0052 |
| Elapsed Time (days) | | | | |
| Measured Bleed (grams) | | | | |
| 5. Control Shell - | 28 | 63 | 86 | 126 |
| (follows typical pattern) | 0.037 | 0.066 | 0.087 | 0.125 |
| Elapsed Time (days) | | | | respectively |
| Measured Bleed (grams) | | | | |

It was concluded that the weight gain of the filter papers indicates that coating the inside of a standard mammary shell with a barrier elastomer rubber substantially deceases the migration of silicone gel through the shell membrane.

What is claimed is:

1. A prosthesis for subcutaneous implantation in a patient comprising a flexible sac and a silicone gel contained within said sac, said sac being comprised of a silicone elastomer wall between 0.05 mm and about 0.2 mm in thickness, said wall comprising a layer of silicone elastomer which substantially impedes the migration of said silicone gel through said wall and has a weight increase of less than 10% when tested in accordance with ASTM D471 using a dimethylpolysiloxane test gel having 300 centistoke viscosity, and being at least 0.025 mm in thickness.

2. The prosthesis of claim 1 wherein the silicone elastomer of said wall is a reaction product of diphenylpolysiloxane and dimethylpolysiloxane, said product having from about 8 to about 50 mole percent diphenylpolysiloxane substituents.

3. The prosthesis of claim 1 wherein the silicone elastomer is a reaction product of methyl 3,3,3-trifluoropropylpolysiloxane and dimethylpolysiloxane, said product having at least 90 mole percent methyl 3,3,3-trifluoropropylpolysiloxane substituents.

4. The prosthesis of claim 1 wherein the silicone elastomer is comprised of a reaction product of methylphenylpolysiloxane and dimethylpolysiloxane, said product having from about 15 to about 50 mole percent methylphenylpolysiloxane substituents.

5. A prosthesis for subcutaneous implantation in a patient comprising a flexible sac and silicone gel contained within said sac, said sac being comprised of a composite wall comprising at least two layers of silicone elastomer and being between about 0.05 and about 0.2 mm thick, one of said layers comprising a silicone elastomer which substantially impedes the migration of the silicone gel through said sac and has a weight increase of less than 10% when tested in accordance with ASTM D471 utilizing a dimethylpolysiloxane test gel having a 300 centistoke viscosity, and is at least about 0.025 mm in thickness.

6. The prosthesis of claim 5 wherein the layer of said composite wall having a change in weight of less than 10% when tested in accordance with ASTM D471, is between about 0.025 mm and 0.05 mm in thickness.

7. The prosthesis of claim 5 wherein the layer of said composite wall having a change in weight of less than 10% when tested in accordance with ASTM D471 is a reaction product of diphenylpolysiloxane and dimethylpolysiloxane, said product having from about 8 to about 30 mole percent diphenylpolysiloxane substituents.

8. The prosthesis of claim 5 wherein the layer of said composite wall having a change in weight of less than 10% when tested in accordance with ASTM D471, is a reaction product of methyl 3,3,3-trifluoropropylpolysiloxane and dimethylpolysiloxane, said product having not less than 90 mole percent methyl 3,3,3-trifluoropropylpolysiloxane substituents.

9. The prosthesis of claim 5 wherein the layer of said composite wall having a change in weight of less than 10% when tested in accordance with ASTM D471 is a reaction product of methylphenylpolysiloxane and dimethylpolysiloxane polymers, said product having at least 30 mole percent methylphenylpolysiloxane substituents.

10. A silicone gel-filled silicone rubber article possessing a reduced tendency to exhibit surface-bleed comprising
(A) a flexible container of silicone rubber consisting essentially of a cross-linked gum of polydimethylsiloxane, said container being filled with
(B) a silicone gel composition consisting essentially of a silicone gel of cross-linked polydimethylsiloxane, there being
(C) an essentially continuous barrier layer of a filler-containing composition consisting essentially of fluorine-containing organopolysiloxane situated between the interior of container (A) and the gel composition of (B), said barrier layer being coated on the interior wall of container (A).

11. A silicone gel-filled silicone rubber article possessing a reduced tendency to exhibit surface-bleed comprising:
(A) a flexible container of fluorosilicone rubber consisting essentially of a cross-linked gum of fluoroalkylpolysiloxane, said fluoroalkylpolysiloxane consisting essentially of fluoroalkylsiloxane units and non-fluorine-containing siloxane units, there being less than 10 mole percent, based upon the total moles of siloxane units present, of non-fluorine-containing siloxane units in said fluoroalkylpolysiloxane, said container being filled with
(B) a silicone gel composition consisting essentially of a silicone gel of cross-linked polydimethylsiloxane.

12. A silicone gel-filled silicone rubber article possessing a reduced tendency to exhibit surface-bleed comprising
(A) a flexible container of silicone rubber consisting essentially of a cross-linked gum of polydimethylsiloxane, said container being filled with
(B) a silicone gel composition consisting essentially of a silicone gel of cross-linked polydimethylsiloxane, there being
(C) an essentially continuous barrier layer of a composition consisting essentially of fluorine-containing organopolysiloxane situated between the interior of container (A) and the gel composition of (B), said barrier layer being coated on the interior wall of container (A).

* * * * *